United States Patent [19]

Epstein et al.

[11] 4,299,234

[45] Nov. 10, 1981

[54] FETAL HEART RATE MONITOR APPARATUS AND METHOD FOR COMBINING ELECTRICALLY AND MECHANICALLY DERIVED CARDIOGRAPHIC SIGNALS

[75] Inventors: Paul Epstein, Brookline; John S. Ballas, Jr., Newton; Joseph M. Van Horn, Cambridge; John J. Mandler, Jr., Allston, all of Mass.

[73] Assignee: Brattle Instrument Corporation, Cambridge, Mass.

[21] Appl. No.: 25,720

[22] Filed: Mar. 30, 1979

[51] Int. Cl.³ .............................................. A61B 5/04
[52] U.S. Cl. ................................................. 128/698
[58] Field of Search ............... 128/661, 663, 689, 698, 128/706, 709

[56] References Cited

U.S. PATENT DOCUMENTS

| 3,561,430 | 2/1971 | Filler, Jr. et al. | 128/661 |
| 3,606,879 | 9/1971 | Estes | 128/661 |
| 3,811,428 | 5/1974 | Van Horn et al. | 128/698 |
| 3,858,574 | 1/1975 | Page | 128/689 |
| 3,982,528 | 9/1976 | Phillipps | 128/661 |

Primary Examiner—William E. Kamm
Attorney, Agent, or Firm—David A. Rich

[57] ABSTRACT

Apparatus and method for continuously monitoring the fetal heart rate simultaneously using ultrasonic and electrocardiographic signals. The signals are continuously processed to provide an improved output fetal heart rate indication in terms of better continuity and accuracy.

12 Claims, 17 Drawing Figures

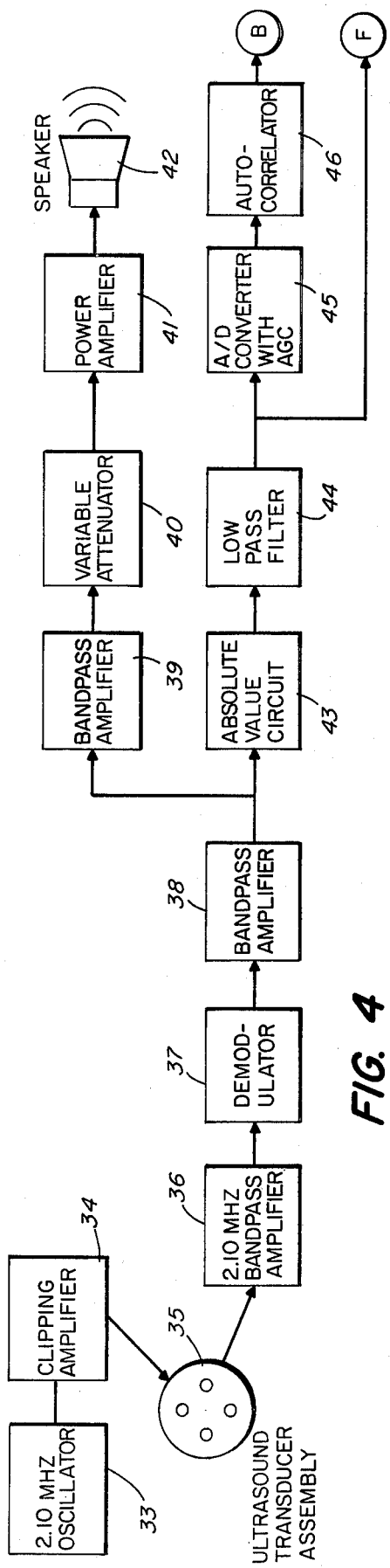
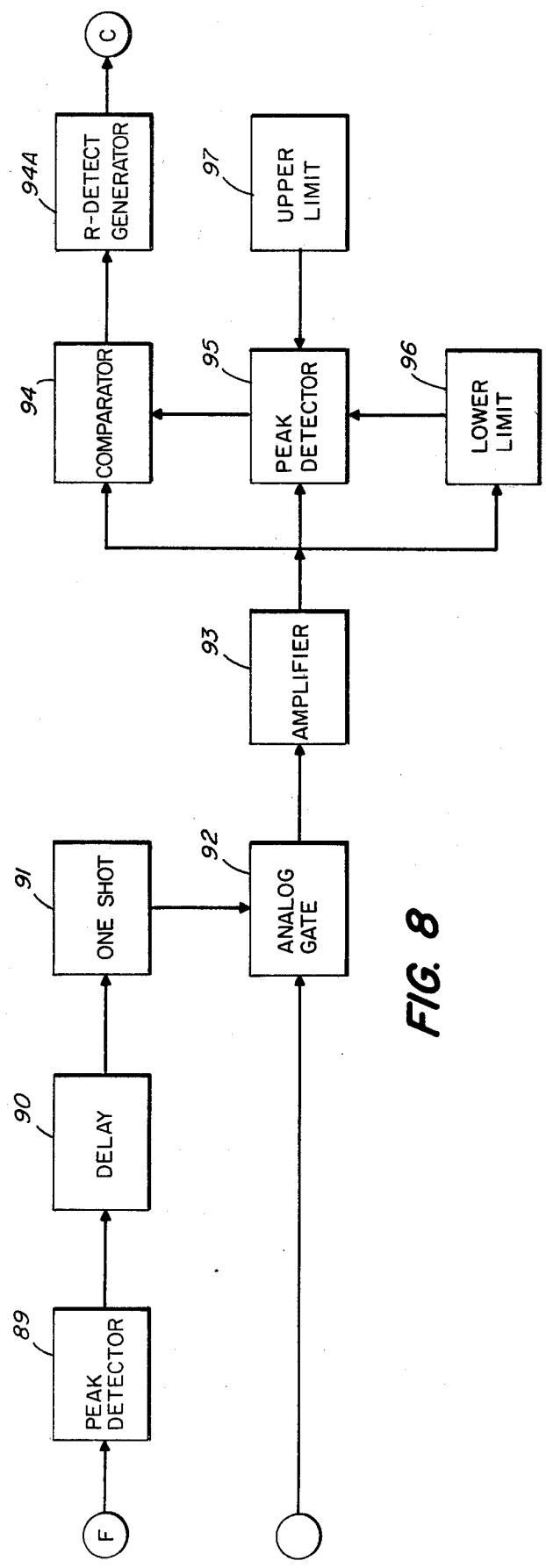
FIG. 4
FIG. 8

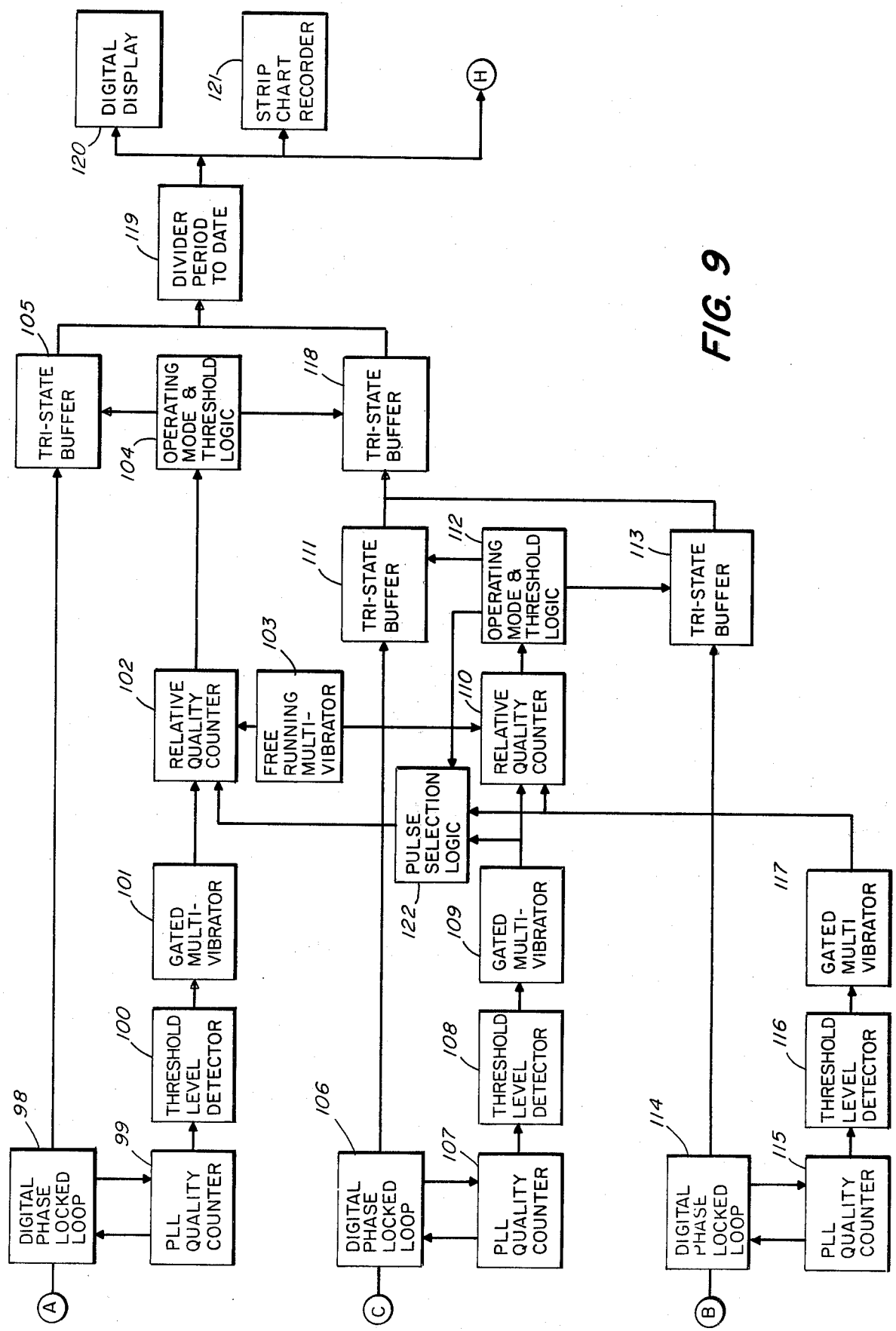

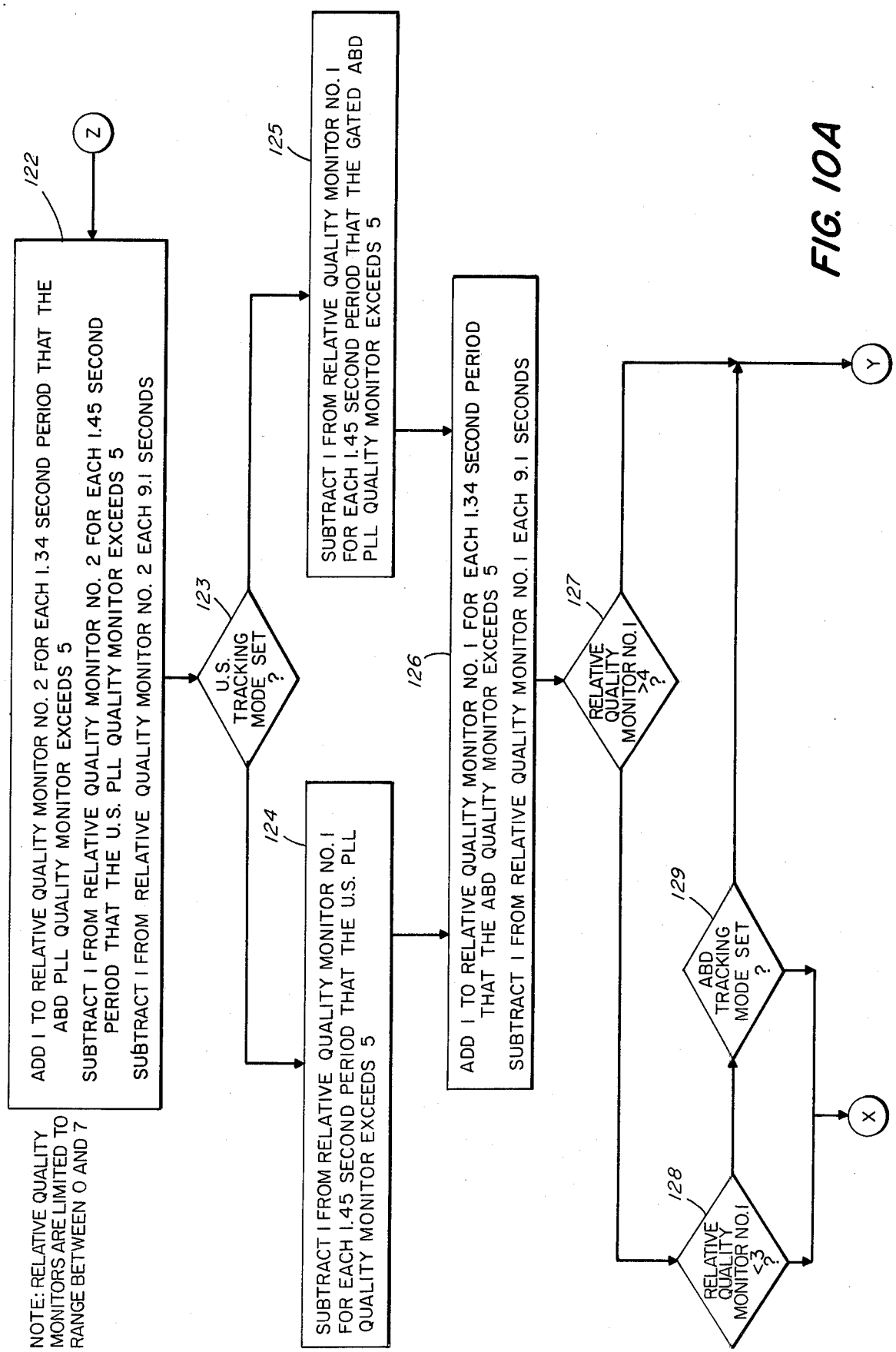

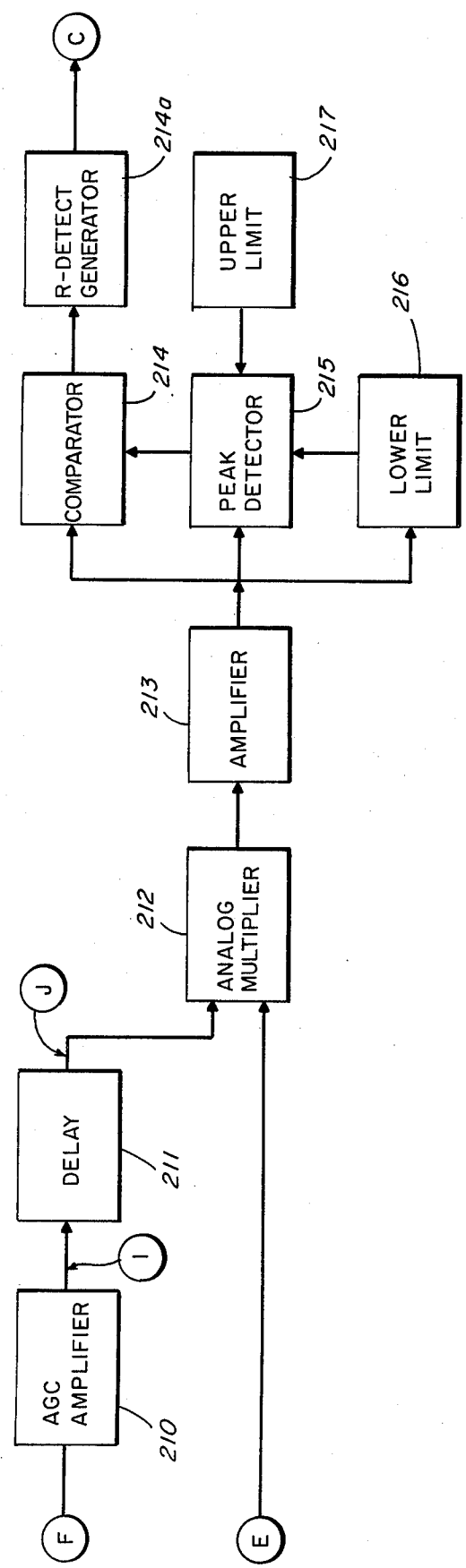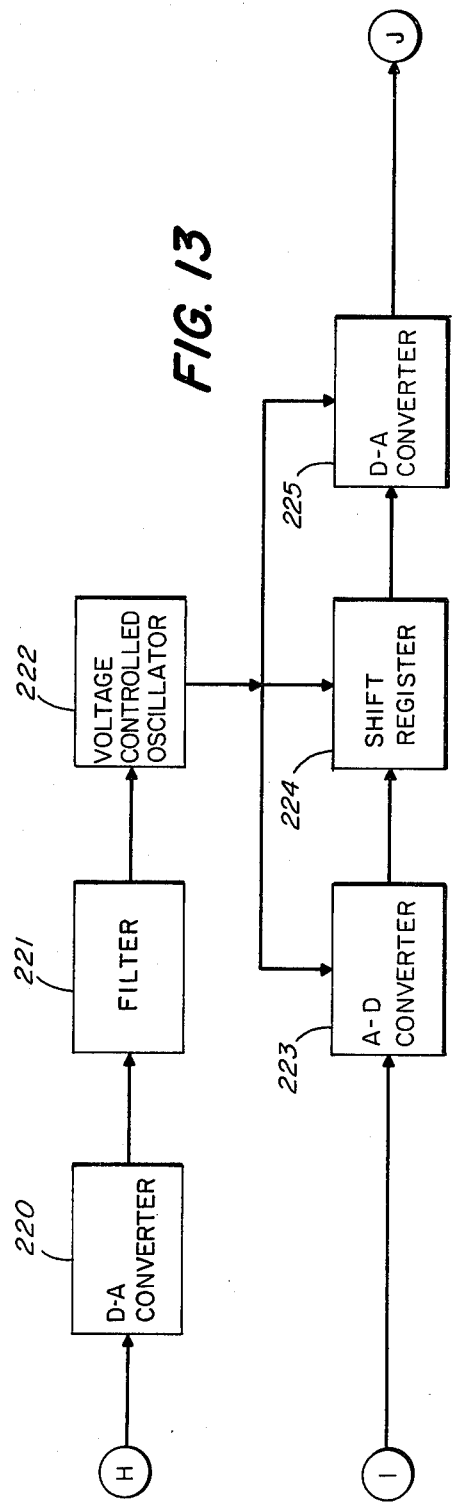
FIG. 12
FIG. 13

FETAL HEART RATE MONITOR APPARATUS AND METHOD FOR COMBINING ELECTRICALLY AND MECHANICALLY DERIVED CARDIOGRAPHIC SIGNALS

BACKGROUND OF THE INVENTION

The present invention related to monitoring biological signals. More particularly the invention relates to continuously monitoring the fetal heart rate.

PRIOR ART

It has long been known that electrical signals associated with the motions of the heart can be directly derived through electrodes connected to a patient and an electrocardiograph instrument to produce a display of an electrocardiographic, ecg, signal indicative of the heart motions. More recently electrocardiographic fetal heart rate, FHR, monitor, FHRM instruments have been developed for providing a signal continuously indicative of the fetal heart rate. Such an instrument is described and illustrated in U.S. Pat. No. 3,811,428, entitled Biological Signals Monitor, issued May 21, 1974 to Van Horn et al. and assigned to the present Assignee. That U.S. Pat. No. 3,811,428 is hereby expressly incorporated herein by reference as an integral part of this disclosure and specification.

Alternatively prior fetal heart rate monitoring practice includes the use of sonar-like radiant ultrasonic energy to produce a mechanical cardiographic, mcg, from which to sense the motion of the fetal heart and provide an output signal indicative of the fetal heart rate. Such an instrument is described and illustrated in U.S. Pat. No. 3,982,528, entitled Apparatus for Refining Signals Derived from Fetal Heartbeats, issued Sept. 28, 1976, to Patrick G. Phillipps and assigned to the present Assignee. That U.S. Pat. No. 3,982,528 is hereby expressly incorporated herein by reference as an integral part of this disclosure and specification.

Frequently both signal methods described above are incorporated in a single instrument such that the operator has an exclusive choice of one or the other depending upon existing conditions. It has been found that neither the ecg or mcg generated FHR signals 100% of the time. At a given time for a given patient, the probability of the presence of a true fetal heart rate signal ranges between 50 to 80%. This fact tends to reduce the usefulness of such prior fetal heart rate monitors. It is widely understood that the technique implied above is broadly useful for prenatal fetal heart rate monitoring during the prenatal period extending, most particularly, through labor. It appears that a substantial increase in the quality and continuity of fetal heart rate signals would significantly increase the use of the FHRM as a diagnostic tool.

SUMMARY OF THE INVENTION

The apparatus and method of the invention indeed significantly improves fetal heart rate monitoring by continuously processing the mcg and ecg signals simultaneously to display both signals after processing or to provide a single, continuous FHR signal derived from the better of either the ecg or mcg signals and/or interaction between them. The ecg signal is normally preferred, if it is "good", because it is more stable and more accurate.

In the preferred mode therefore a selection process takes place biased in favor of the ecg signal. A selection process is employed to determine the following:
1. To determine the presence or absence of a heart beat,
2. To determine the period between heart beats from which to derive the heart rate,
3. To verify each signal as being true,
4. To select the ecg derived FHR signal if it is as "good" as or "better" than the mcg signal, or
5. To select the mcg signal if the ecg signal is sufficiently degraded and the mcg signal is sufficiently "good" to be useful.

The output fetal heart rate signal may be significantly enhanced by processing the two signals together to provide other intermediate signals available for selection as an output signal, for verifying the presence of a true signal or for verifying and more accurately presenting the instantaneous fetal heart rate. By virtue of continuous crosscorrelation, in addition to autocorrelation of each signal, of the two signals a whole range of functions may be introduced. These include, without limitation:
1. Varying one signal relative to the other in time,
2. Algebraically adding the signals together,
3. Multiplying the signals together,
4. Comparing the signals,
5. Further processing the signals with other intermediate signals,
6. Disabling one or more selected signal channels, and
7. Performing any other function appropriate to available input, intermediate and output signals.

In the preferred modes, the present invention is implemented by incorporating modifications of the apparatus and methods described and illustrated in the above-identified '528 and '428 patents and further processing for selecting, as an output fetal heart rate signal, the preferred, i.e., "the best", output fetal heart rate signal.

While the discussion above relates to the preferred modes for human patients it is apparent that the invention is applicable to a wide range of biological objects. Further, the input signals derived from the biological object may differ in character and number from those described above.

DETAILED DESCRIPTION OF THE PREFERRED MODES OF THE INVENTION

What follows is a description of the preferred modes of the invention, taken in connection with the accompanying drawings, and its scope will be defined in the appended claims.

IN THE DRAWINGS:

FIG. 4 is a schematic circuit block diagram illustrating in greater detail the mcg signal processing circuit of the monitor in FIG. 2;

FIG. 8 is a schematic block diagram illustrating a modification of the monitor in FIGS. 2–6 for interprocessing the ecg and mcg signals for producing an intermediate signal;

FIG. 9 is a schematic block diagram of a selection circuit for continuously deriving an output fetal heart rate signal selected from one of the ecg, mcg or intermediate signals;

Figure 10B:
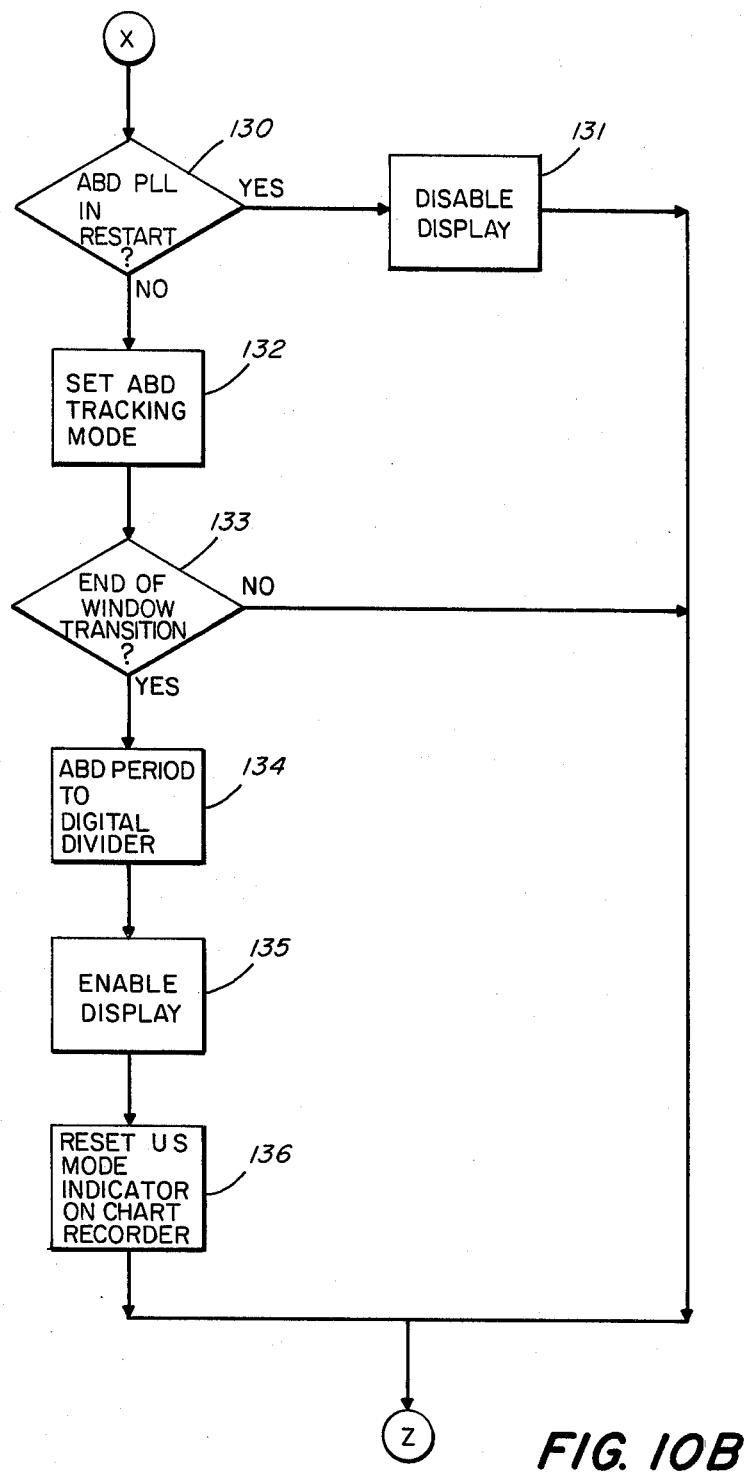
Figure 10C:
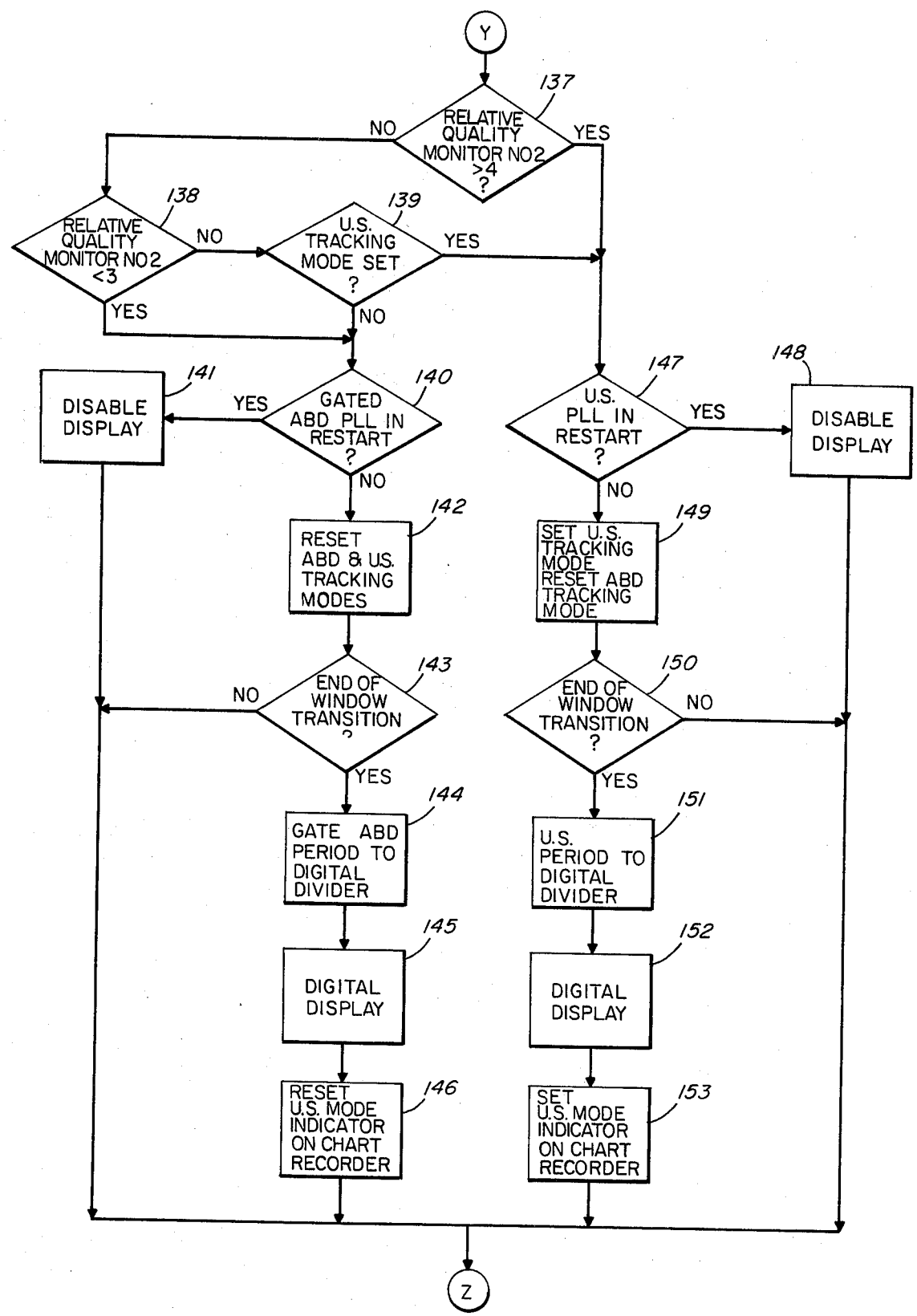
Figure 11:
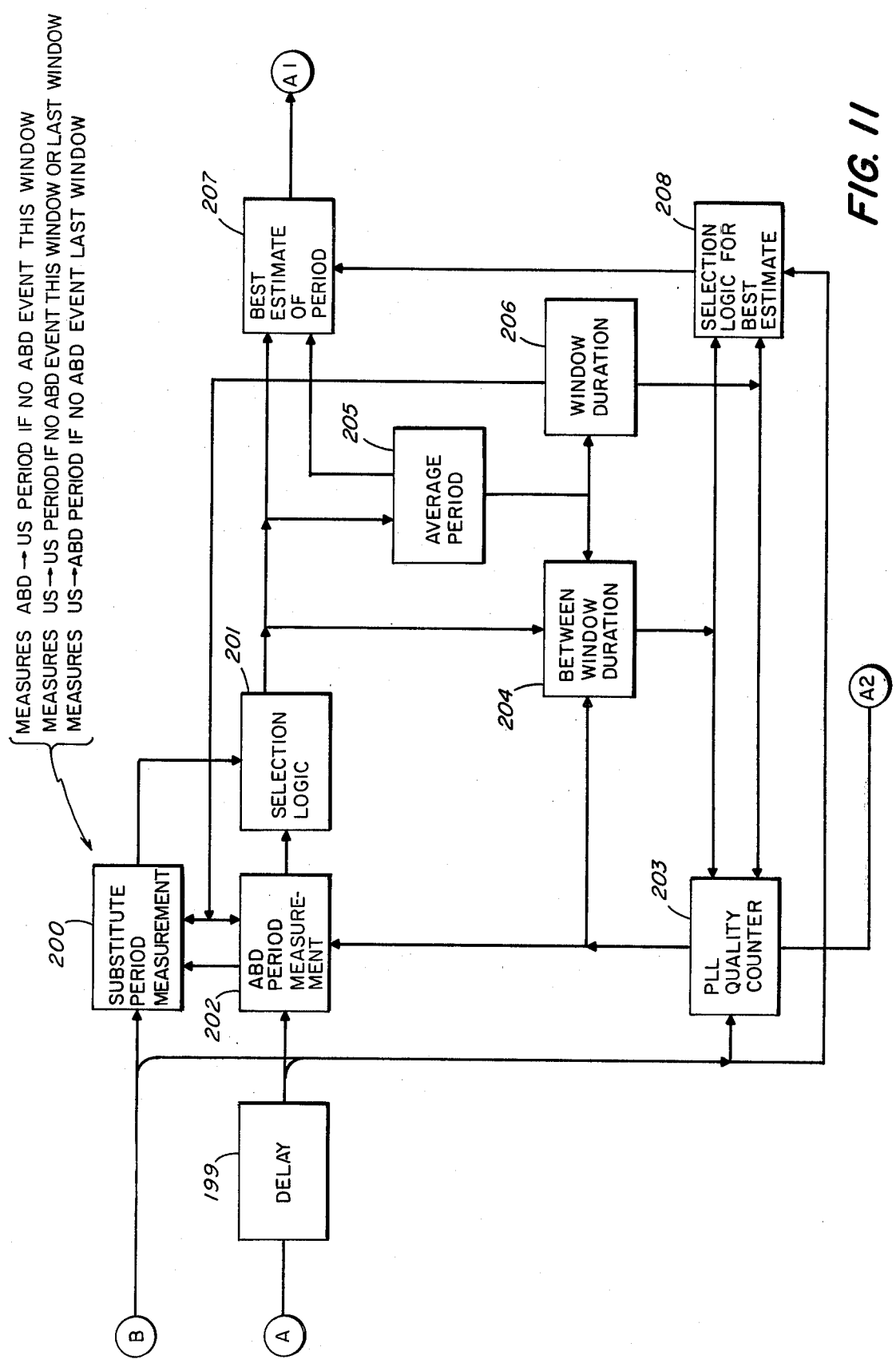
Figure 14:
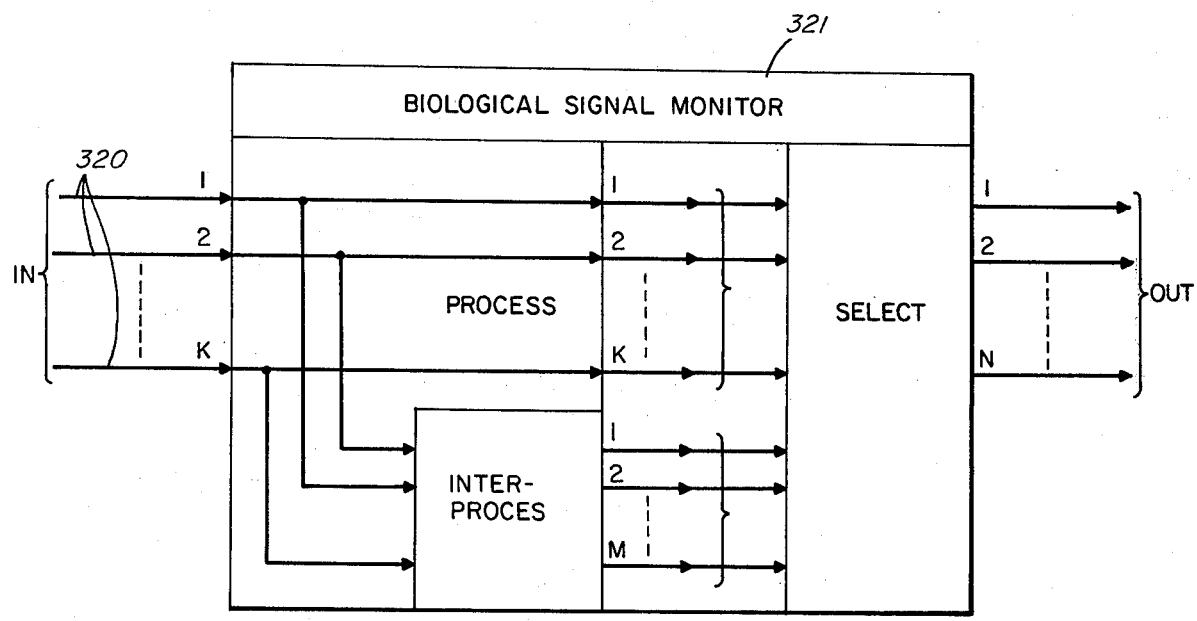
Figure 15:
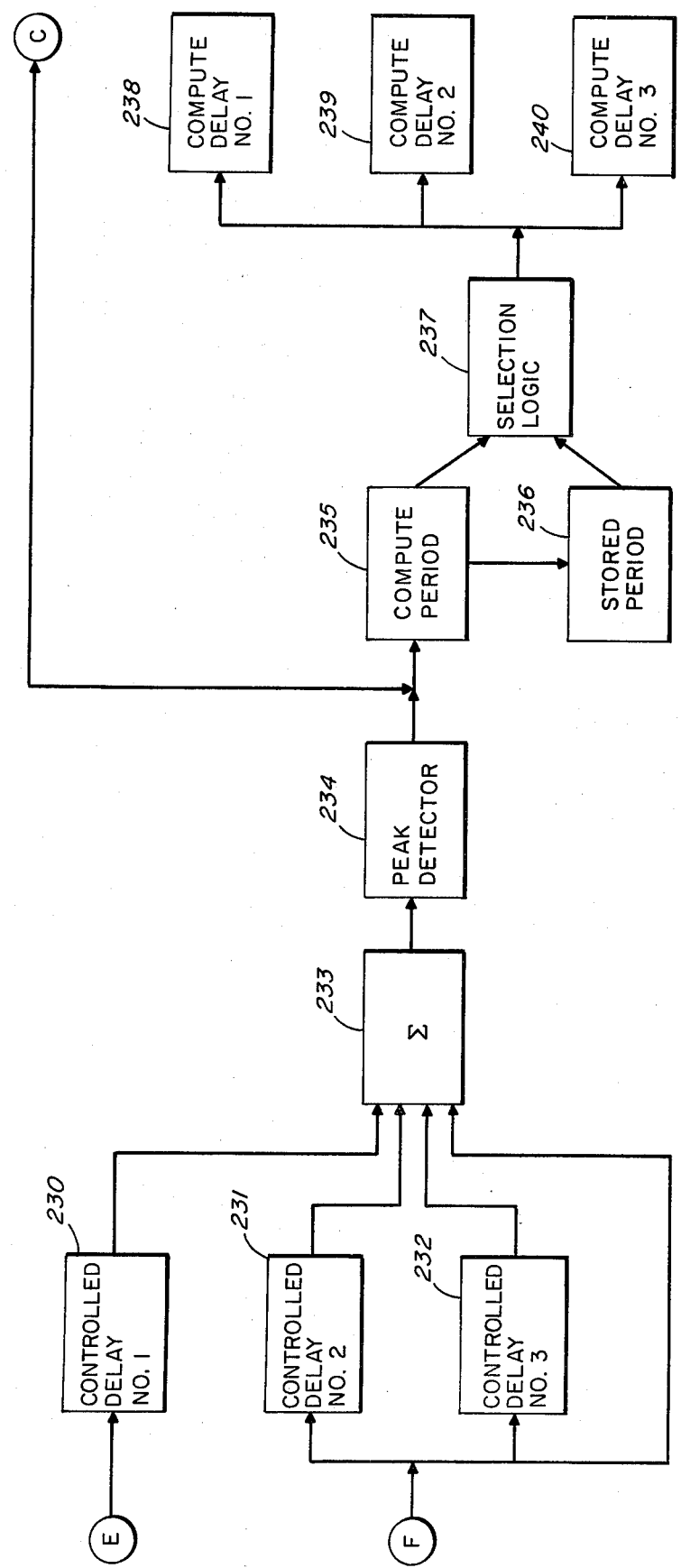

FIGS 10A–10C comprise a logic sequence, schematic block diagram illustrating the operation of the monitor in FIGS. 2–6 as modified in FIGS. 8 and 9;

FIG. 11 is a schematic circuit block diagram of a modification of the monitor of FIGS. 2–6 for interlacing a mcg derived FHR signal in place of a missing ecg signal;

FIG. 12 is a schematic, circuit block diagram of a modification of the monitor in FIGS. 2–6 effectively to multiply the ecg and mcg signals to produce an enhanced FHR signal;

FIG. 13 is a schematic, circuit block diagram of a modification of the monitor in FIGS. 2–6 to vary the relative time of occurrence of the ecg and mcg signals; and FIG. 14 is a schematic circuit block diagram of a monitor for biological signals;

FIG. 15 is a schematic circuit block diagram of a modification of the monitor in FIGS. 2–6 for adding ecg and mcg signals to produce an enhanced FRH signal.

DESCRIPTION AND OPERATION OF THE FETAL HEART RATE MONITOR IN FIGS. 1–7

Figure 1:
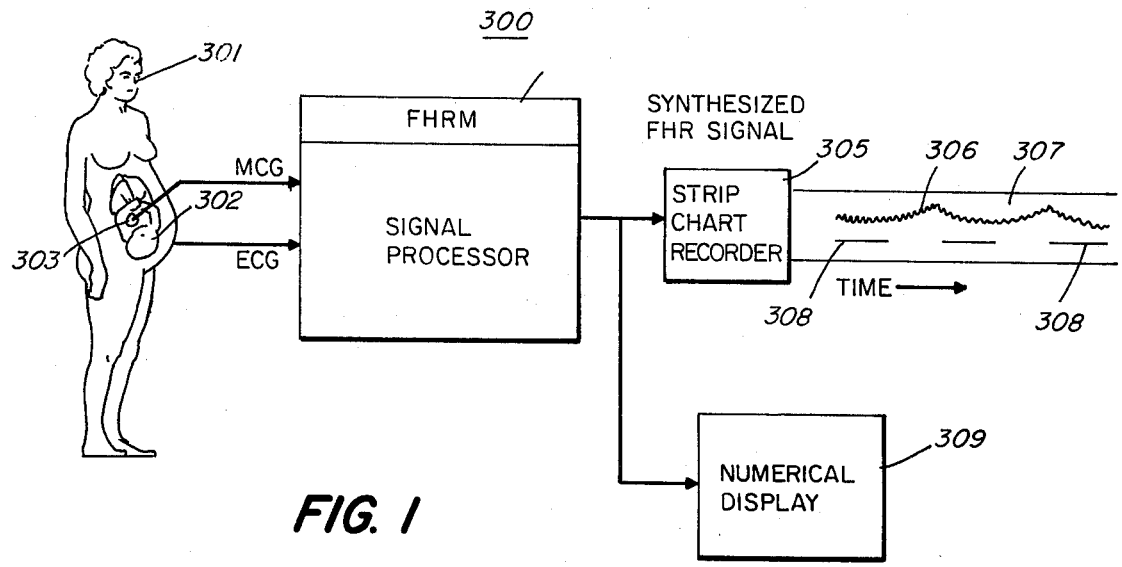
FIG. 1 is a schematic block diagram of a fetal heart rate monitor embodying the invention.

Referring now to the drawings, and with particular reference to FIG. 1, there is here illustrated a Fetal Heart Rate Monitor, FHRM, embodying a preferred mode of the invention. A fetus-carrying female person is coupled to a FHRM. A mechanical cardiographic, mcg, signal representative of the recurrent fetal cardiac fluctuations, here an ultrasonic, Doppler, sonarlike signal, and an electrocardiagraphic, ecg, signal are each coupled from the mother and fetus to an FHRM. An output synthesized Fetal Heart Rate, FHR, signal is shown as a single, substantially continuous, tracing on a strip chart and/or as a digital display. The ecg/FHR signal is derived from the ecg and the mcg/FHR signal is derived from the transmitted and reflected ultrasonic, e.g., of the order of megahertz, energy to and from the fetal heart, respectively.

The mother and fetus, as coupled to and from the FHRM and recorder, is generally indicated at 300. The mother 301 carrying a fetus 302 and fetal heart 303 are shown coupled to a FHRM 304 and strip chart recorder 305 to produce an FHR signal tracing 306 on a recording chart 307. The underlining 308 indicates the time during which the FHR is indicative of the mcg. At all other times the tracing is either an ecg/FHR signal or blank, i.e., none at all. The FHR is also shown in a digital display 309. In operation the input signals are continuously monitored and processed. In the case of the mcg, the transmitted and received mcg signals are heterodyned to produce a Doppler difference signal to provide the mcg signal. The mcg signal is derived from an electrical signal generated in the monitor 304 which is converted by a transducer into a beam of sonic energy transmitted to the fetal heart and receives the reflected sonic energy from the fetal heart. The received energy is then converted into an electrical signal representative of the received sonic energy. The transmitted and received signals are then heterodyned to produce an electrical different Doppler frequency mcg signal.

In the system as described and illustrated in FIGS. 2–7, inclusive, the mcg and ecg signals are processed to determine the best estimate of the last period between heart beats. A decision is then made as to which is the better signal indicative of a true FHR most accurately. Having chosen the best estimated period it is then converted to an FHR signal which is either displayed numerically in the display 309, with for example light emitting diodes or liquid crystal display, and/or coupled to a strip chart recorder to produce the tracing 306.

In another mode of the preferred embodiment an intermediate signal is produced or derived from processing the ecg and mcg signals by for example, without limitation, comparing, correlating, adding, multiplying and/or varying the relative time of occurrence between them. The selection circuit then chooses the best one of the processed ecg, mcg or intermediate signals derived from the input signals, and converted to a FHR signal. The FHR signal appears as a substantially continuous tracing or numerical display.

The system in both modes of operation is biased in the favor of the ecg/FHR signal. Other things being equal, the ecg derived FHM signal is preferred. The ecg signal is fundamentally less confusing because of the clear presence of the R wave which provides an accurate and recognizable or easily detectable point in the cardiac cycle; thereby enabling a more accurate and unambiguous measure of the R to R period. In contrast, there are so many motions of the heart and other vessels, which contribute to the Doppler signals, that the mcg signals derived in response to such motions tend to be ambiguous. The ecg mode is also called "abdominal or ABD" because of the preferred electrode position on the mother. The mcg mode is also termed "ultrasound" in the art because of the preferred frequency of the sonic energy. The term mechanical as used herein, without limitation, characterizes mechanically derived energy in solid and/or fluid, i.e., liquids and gases, media.

Selection

Figure 2:
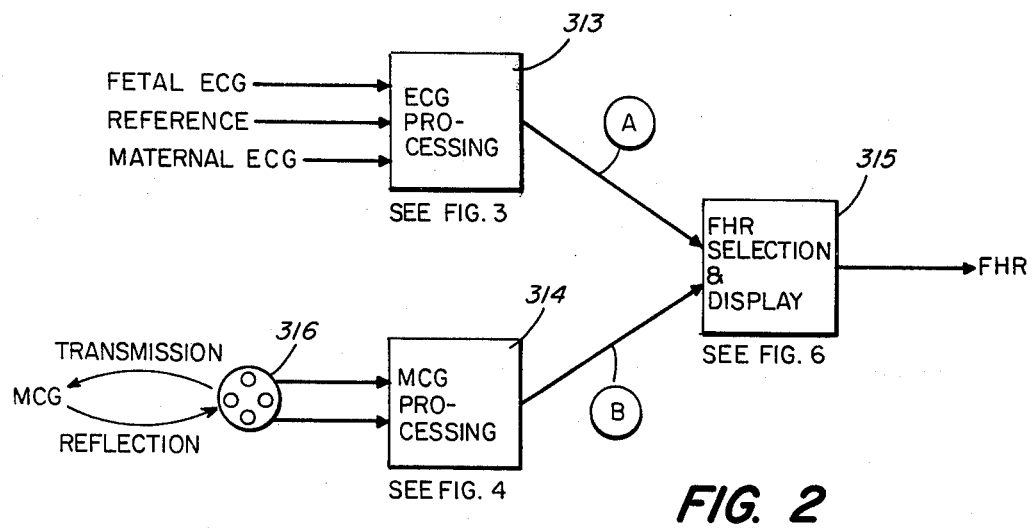
FIG. 2 is a more detailed schematic block diagram illustrating a mode of operation of the monitor in FIG. 1 for continuously selecting either the ecg or the mcg signal for producing an output, synthesized fetal heart rate signal.

In FIG. 2 a FHRM is shown with an ecg signal channel and an ultrasound or mcg channel coupled to a selection circuit. The ecg signal is coupled through abdominal electrodes coupled to the monitor. The mcg signal is coupled from the fetal heart through a transducer, which converts sonic energy to electrical signals. The ecg and mcg signals are coupled to a selection circuit to derive an output FHR signal. In FIG. 2 the fetal and maternal ecg signals are shown coupled to an egg processor 313. The processor output A is coupled to the selection and display circuit 315. The mcg signal is coupled to and from the fetal heart through a transducer 316 which converts electric signals from a mcg processor 314 into a transmitted sonic beam. Reflected sonic energy from the fetus is converted in the transducer 316 into electrical signals coupled to the processor 314. The output signal B is coupled to the selection circuit 315 to derive an output FHR signal representative of the better of the fetal ecg or mcg signals.

Figure 3:
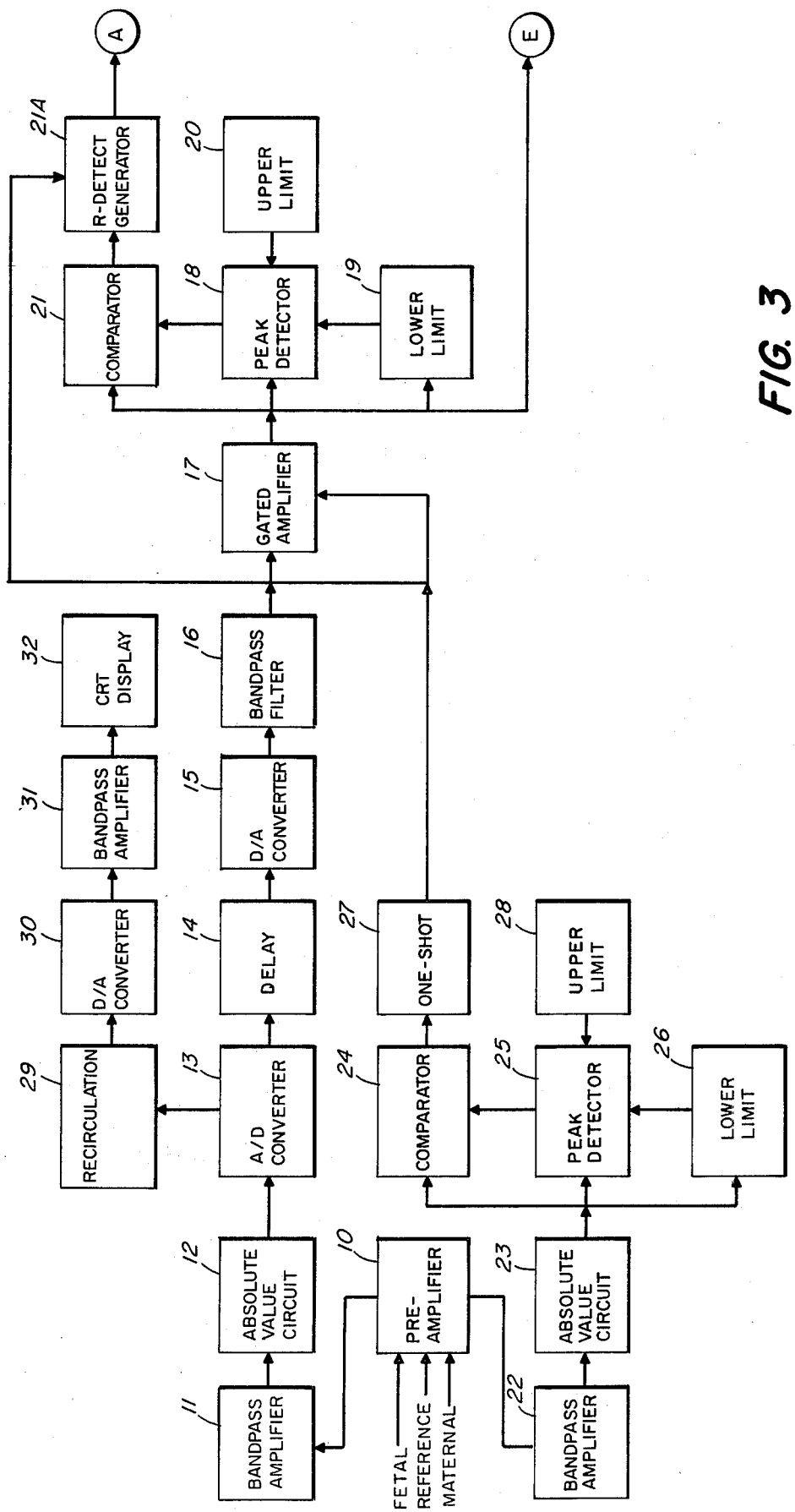
FIG. 3 is a schematic circuit block diagram illustrating in greater detail the ecg signal processing circuit of the monitor in FIG. 2.

The ecg processor in FIG. 3 represents a variation of that described in the '428 patent cited above. FIG. 3 corresponds with ecg processor 313 in FIG. 2.

Electrodes are placed on the mother to provide fetal and maternal ecg input signals to a preamplifier 10. The preamplifier includes two independent, isolated preamplifiers, one for the fetal ecg signal and the other for the maternal ecg signal. The fetal ecg signal is routed from preamplifier 10 through a bandpass amplifier 11, which limits the band width and rejects 50 or 60 cycle power line frequencies by the means of a notch filter. The output of the bandpass amplifier is coupled to an absolute value circuit 12 which puts all of the peaks of the fetal and maternal ecg signals on the same polarity for subsequent filtering and detection of the occurrence of a heart beat. The output of circuit 12 is routed to an analogue to digital, A to D, converter 13 where the analog ecg signal is converted to a digital signal. Outputs from the A to D converter go to a circulation storage register 29 which provides non-fade display capability for a cathode ray tube. The other output of the A to D converter 13 goes to a digital shift register, a delay circuit 14. This delays the signal by approximately 32 milliseconds. The delayed signal is then routed to a D to A converter 15 where the analog signal is reconstituted and then passed on to band pass filter 16 for smoothing.

The output of the band pass filter is then routed to Gated amplifier 17. This amplifier is gated off by a maternal gate signal from one-shot 27. The purpose of this is to delete maternal signals form the fetal channel which contains both fetal and maternal ecg signals. The output of the gated amplifier 17 goes simultaneously to peak detector 18 lower limit 19 and comparator 21. These three combined with the upper limit 20 comprise the circuitry by which the R wave is detected. Lower limit 19 receives an input from gated amplifier 17 and determines the average noise level of the signal. It then sets a lower limit threshold at some point above the peak noise level to assure that the machine is not going to respond to noise peaks and interpret them as being fetal QRS complexes. The upper limit is established by a resistor divider to prohibit the peak detector from staurating on noise.

The peak detector detects the maximum amplitude within the range of lower to upper limits and establishes a threshold level for acceptable R waves. This threshold is provided to comparator 21 and if any signal from the gated amplifier 17 exceeds this threshold, the comparator will output a signal to R-detect generator 21A. This generator detects fetal signals which have been partially detected by the leading edge of the maternal gate. Its output, signal A indicates that an R wave has been detected. Meanwhile, the maternal channel signal has undergone a similar series of processing except for the digital conversions and the delay. The maternal signal output from the preamplifier 10 is filtered and the power frequencies notched out by band pass amplifier 22. Its output is routed to absolute value circuit 23 where the signal is rectified. The output of the absolute value circuit 23 is then routed to peak detector 25, the lower limit 26, and the comparator 24. This together with upper limit 28 represents a QRS detect circuit. It operates much the same as that previously described for the fetal detect signal in FIG. 1. The output from the comparator triggers one shot 27, and this one shot has a duration which will exceed the typical duration of the material QRS complex to assure that when the gated amplifier 17 is gated off, the entire maternal QRS complex is deleted from the fetal channel. The output of the recirculation storage register 29 is routed to D to A converter 30 where the analog signal is reconstituted and then routed to band pass amplifier 31. Here the signal is amplified and filtered. It is then routed to CRT display 32 for display on a cathode ray tube.

FIG. 4 is a mcg signal processor as described in patent '528, cited above. A 2.1 megahertz oscillator 33 generates an electrical signal, passes it to clipping amplifier 34 where it is clipped to a stable signal of 10 volts peak to peak. This signal is then transferred to the ultrasound transducer assembly 35 where it is beamed into the uterus. Reflections are detected by the transducer assembly, converted into an electrical signal by the ultrasound transducer assembly and subsequently amplified by 2.10 megahertz band passed amplifier 36. The output is then demodulated 37 and forwarded to an audioband pass amplifier 38. The output of this amplifier is routed to band pass amplifier 39 and simultaneously to absolute value circuit 43. The band pass amplifier 39 is the first circuit in a chain which results in an audible sound representitive of the detected Doppler events. The output of 30 goes to variable attenuator 40 which allows volume control from the front panel. The output of 40 goes to power amplifier 41 subsequently to speaker 42 for the audible sound. The rectified signal output from absolute value circuit 43 is filtered in low pass filter 44 and converted to a digital signal in 45. The A to D converter 45 has automatic gain control to normalize the signal amplitude. This signal is then routed to an autocorrelator 46, described in detail in '528. Output from the autocorrelator is a pulse B which is used as an input to a digital phase locked loop in the automobile switching. The output from low pass filter 44 is combined with a signal from the abdominal signal processing chain to generate an enhanced signal for use in a third channel of the automode switching.

Figure 5:
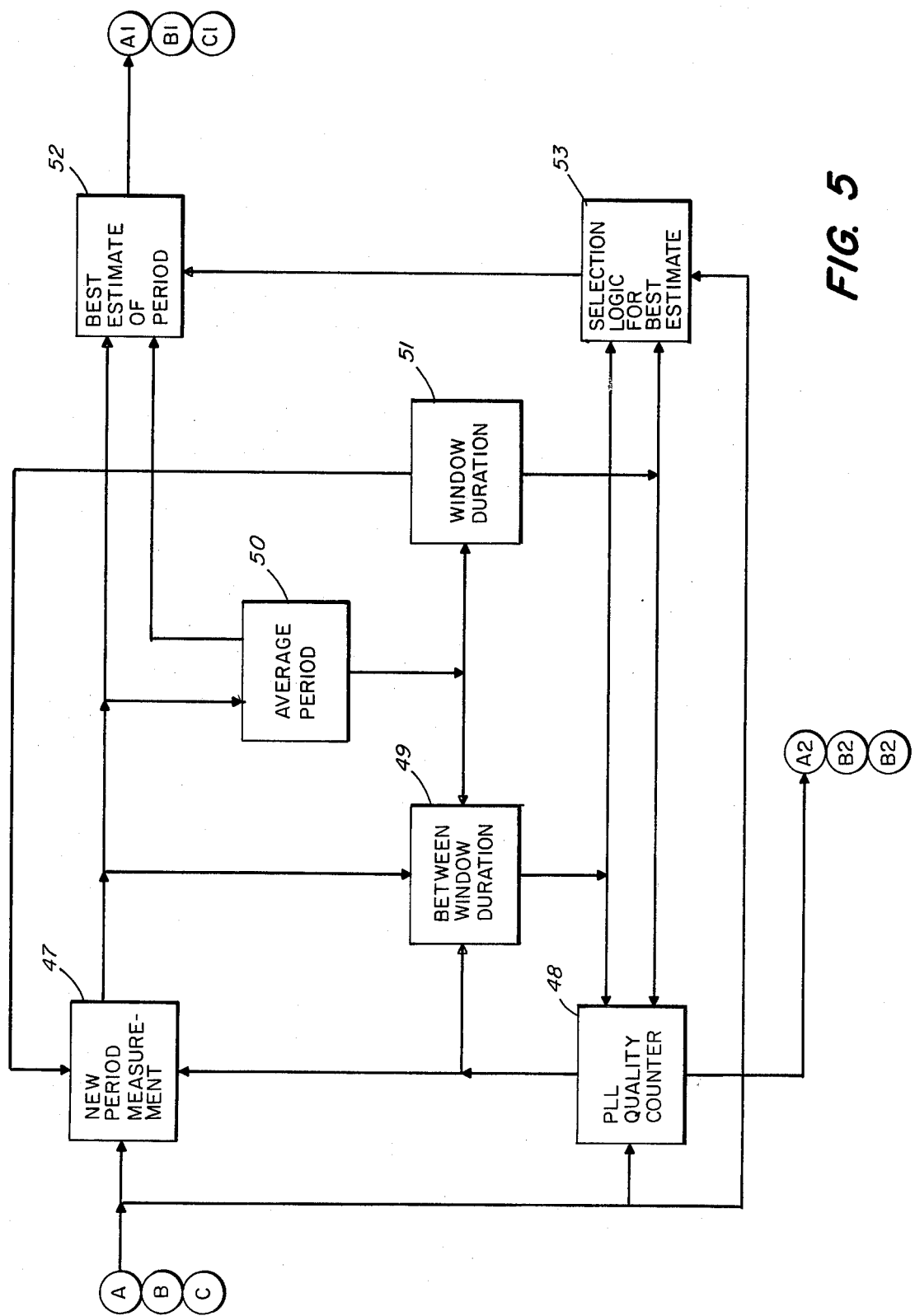
FIG. 5 is a detailed, schematic circuit block diagram of a phase lock loop as used in the preferred embodiments as indicated below.

The phase lock loop and quality counter circuit in FIG. 5 is a revision of FIG. 10 in U.S. Pat. No. '428. Basically the input signal A (or B or C) is presented to a new period measurement circuit 47. This circuit contains a counter which counts the period between subsequent A inputs. Input A is also presented to the phase lock loop quality counter 48 and to the selection logic for a best estimate circuit 33. New period measurement is presented to the average period circuit 50 where a new average period is calculated. This average period is then used along with the new period measurement to calculate the between windows duration 49. Average period is also used in conjunction with signal inputs A to either increment or decrement the counter 48. It is incremented by one each time an event is detected between the windows or, if no event is detected within a window, and it is decremented by one-half each time an event is detected within the window. The counter 48 counts up to the number 8, a restart is initiated and it outputs a signal to the new period measurement 47 and the between window duration 49 to cause the phase lock loop to enter a restart condition. In the restart condition the phase lock loop simply ignores all previous information regarding period; it looks for the next two events coming in at A and determines the period of those events, calculates a new average period, between windows durations and window durations. When the phase lock loop is tracking correctly, the phase lock loop quality counter gradually reduces the number it contains until it gets down to zero.

Thus, the phase lock loop quality counter functions as an error counter which determines just how well the phase lock loop is tracking the true input signal at A. Therefore, the output of this counter is an indicator of the quality of the signal in this channel and can be compared with similar signals, developed from phase lock loop circuits associated with other channels and the results combined in a relative quality counter to provide a mechanism for automode switching. This is done and will be explained in FIG. 4 and later in FIG. 6. Output A2 (or B2 or C2) from the phase lock loop quality counter indicates when the phase lock loop quality counter has exceeded a fixed threshold. The output of phase lock loop is developed in best estimate of period 52 which receives data inputs from new period measurement 47, average period 50 and selection criteria from the selection logic for best estimate 53. The new period measurement is a true representation of the actual period only if one event was detected in the present window and one event was detected in the previous window. If this condition is not true then the best estimate of the period is taken to be the average period as developed in 50. Therefore, best estimate of period 52 under control of the selection logic in 53 selects either the new period measurement or the average period to be output as the period measurement A1 (or B1 or C1).

Figure 6:
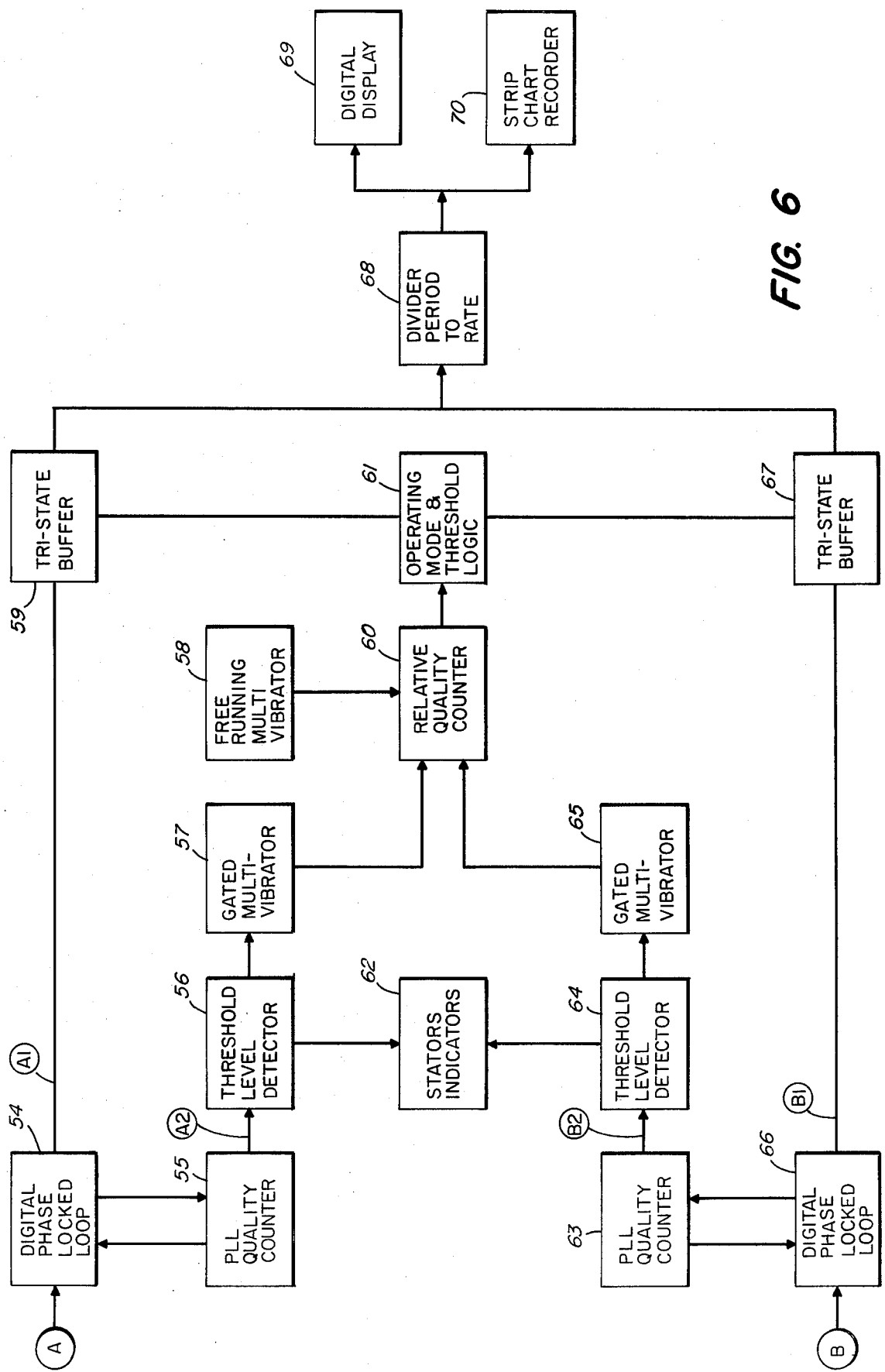
FIG. 6 is a schematic circuit block diagram of the selection circuit of the monitor of FIG. 2 for continuously selecting, either the ecg signal, the mcg signal or none, as an output fetal heart rate signal.

In FIG. 6 the selection circuit or automode switching between the ecg and mcg channels is shown. Input signal A comes from the abdominal signal processing chain in FIG. 3 and the input signal B comes from the ultrasound signal processing chain in FIG. 4. Each of these signals is presented to a specific digital phase lock loop as shown in FIG. 5. These phase lock loops independently track their respective incoming signal and generate a best estimate of the period which in the case of the abdominal channel is shown in FIG. 4 as signal A1. A1 is then routed to the tri state buffer 59 which is controlled by operating mode threshold logic 61, and if selected allows the abdominal period to be the one which is used to calculate the actual fetal heart rate. Similarly, the ultrasound phase lock loop 66 has been tracking the ultrasound signal and its period measurements are presented to tri state buffer 67, which is also controlled by operating mode and threshold logic 61. If the ultrasound has been selected as the best tracking signal then the ultrasound period will be routed through the tri state buffer and used to calculate the fetal heart rate. As previously indicated in the FIG. 3 description, the phase lock loop quality counter output A2 provides the information by which the relative quality of the tracking of abdominal or ultrasound signals can be determined. Signal C is presented to threshold level detector 56, where it is compared to a fixed threshold. If it exceeds that threshold, 56 enables gated multivibrator 57 which generates a series of output pulses as long as it is enabled. The poorer the quality of the abdominal signal, the longer signal A1 will exceed the threshold defined by detector 56. Thus the number of pulses generated by gated multi-vibrator 57 is a measure of the quality of the abdominal signal. The pulse outputs from gated multi-vibrator 57 are then used to decrement relative quality counter 60. Meanwhile, the ultrasound signal has been monitored in a similar fashion. In the ultrasound channel, the phase lock loop quality counter 63 outputs a signal to threshold level detector 64 and if this signal exceeds the fixed threshold it will enable gated multi-vibrator 65 to output a series of pulses which provide a measure of the quality of tracking in the ultrasound channel. The output of gated multi-vibrator 65 is used to increment the relative quality counter 60. To provide a bias in the relative quality counter such that if both channels are tracking equally well, the abdominal channel signal is used as the basis for calculating fetal heart rates, a free running multi-vibrator 58 is used to periodically decrement the relative quality counter 60. Thus if the two channels are tracking at equal quality levels, the free running multi-vibrator will cause the free running multi-vibrator to count down towards zero. The output of the relative quality counter 60 goes to the operating mode and threshold logic 61. This circuit makes a decision based on the data it has received from the quality counter and some prior history as to which channel will be used as the basis for calculating the fetal heart rate. Having made that decision it provides an output to either of the two tri state buffers 59 or 67. Turning one of them on and the other one off. The tri state buffer which is turned on then passes data on to divider period to rate circuit 68. This circuit calculates the fetal heart rate based on the period information presented to it and outputs this fetal heart rate information to digital display 69 and to strip chart recorder 70.

Figure 7:
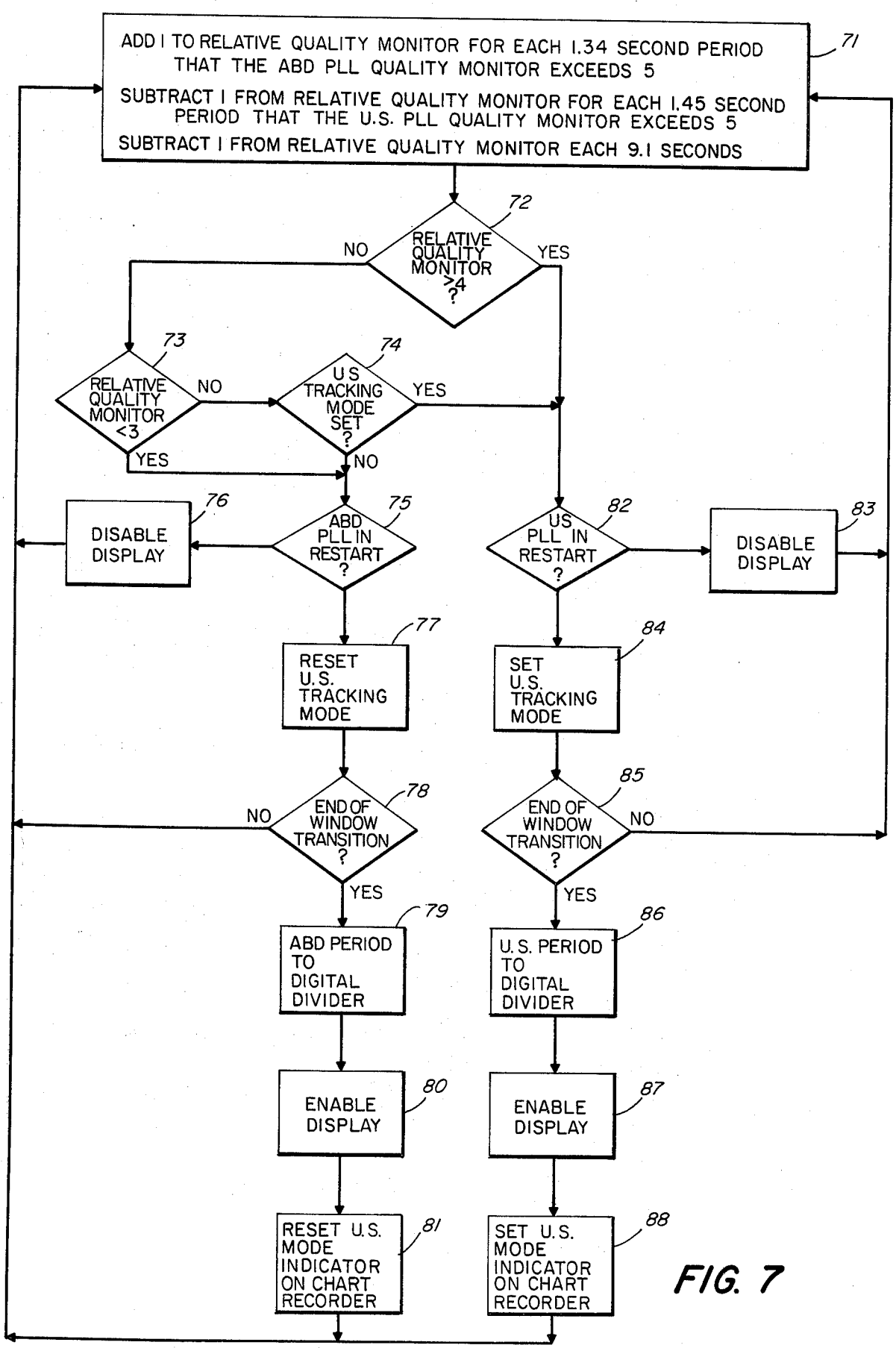
FIG. 7 is a logic sequence, schematic block diagram illustrating the operation of the monitor in FIGS. 2–6.

In FIG. 7 the algorithm is shown for switching between two signal channels, in particular between the abdominal and ultrasound fetal heart signals. Starting at the top of the diagram, block 71 defines the relative quality monitor. This monitor is incremented by one for each one point three four 1.34 second period that the abdominal phase lock quality monitor exceeds five, it is decremented by one for each 1.45 second period that the ultrasound phase lock loop quality monitor exceeds five and it is also decremented by one continuously every 9.1 seconds. Thus for situations where there is poor quality in the abdominal channel, the counter counts away from using the abdominal channel and counts towards using the ultrasound channel as the basis for fetal heart rate determination. Similarly, if there is poor quality in the ultrasound channel, the counter counts away from using the ultrasound channel and towards using the abdominal channel as the basis for fetal heart rate determination. All the while the counter has a bias towards the abdominal by the constant low rate decrementing of one count each 9.1 seconds. After incrementing and decrementing this relative quality monitor, its contents are examined. This starts with block 72 which asks the question, "Is the relative quality monitor greater that 4?" If it is not then we go to block 73 which asks the question, "Is the relative quality monitor less than 3?" If that is true, then the algorithm wants to be in the abdomianl phase lock loop tracking mode. Next, block 75 asks the question, "Is the abdominal phase lock loop in restart?" If it is, then the display is disabled and the algorithm returns to the start. Returning to blocks 72 and 73 if the relative quality monitor is not greater than 4, and is not less than 3 then the algorithm proceeds to block 74, and asks the question, "Is the ultrasound tracking mode set?" If it is, the algorithm wants to be in the ultrasound tracking mode, and proceeds to block 82. Blocks 72, 73 and 74 define a threshold with hysteresis. If the relative quality monitor is greater than 4 then we want to be in the ultrasound tracking mode, if the relative quality monitor is less than 3, then we want to be in the abdominal tracking mode. However, if the relative quality monitor is either 3 or 4, then the preferred tracking mode is the existing tracking mode.

Block 75 asks the question, "Was the abdominal phase lock loop in restart?" If it was not, then the tracking mode is set to the abdominal mode in block 77. Block 78 asks the question "Is the end of window transistion occurring?" If it is not, the algorithm returns to the start and recycles in that loop until the end of window transistion does occur, at which time block 79 calls for the abdominal period as calculated by the abdominal phase lock loop to be transferred to the digital divider. In block 80 and the display is enabled allowing the most recent fetal heart rate data to be written on the chart recorder and digital display. Finally the ultrasound mode indicator on the chart recorder is reset in block 81.

Block 82 asks the question, "Is the ultrasound phase lock loop in restart?" If it is the algorithm calls for the display to be disabled in block 83 and a return to start, recycling in that loop until the restart condition is removed. If the ultrasound phase locked loop is not in restart, block 84 sets the tracking mode to ultrasound. Block 85 then asks the question, "Has the end of window transition occurred?" If it has not then the algorithm would recycle back to the beginning and continue in that loop until the transition does occur. While it cycles in that loop the algorithm is constantly checking the relative quality monitor for any changes that would redirect it to the abdominal tracking portion of the algorithm. When block 85 determines that the end of the window transition is occurring, then block 86 transfers the period information calculated by the ultrasound phase lock loop to the digital divider, block 87 enables the display, and block 88 sets the ultrasound mode indicator on the chart recorder which enables a pen to scribe a line on the chart recorder indicating that the recorded data is derived from the ultrasound channel.

FIG. 8 is a block diagram for range gating the abdominal signal from the ultrasound event. Input F is the processed analog signal from the ultrasound channel. It is peaked detected to indicate the time of occurance of the maximum Doppler shift. This signal is then delayed in block 90 and the delayed signal used to trigger a one shot 91, which will turn on a normally shunt off analog gate 92. Delay 90 and one shot 91 are selected so that the one shot is coincedent in time with the fetal QRS complex. This QRS complex is then gated through to amplifier 93. and lower limit 96. These blocks, in conjunction with the upper limit 97 represent a QRS detect circuit such as described for FIG. 2. The output from comparator 94 is processed through R detect generator 94A whose output is the range gated enhanced abdominal R detect signal C.

Selection ecg, mcg or intermediate signals

The block diagram for switching between three channels is shown in FIG. 9. With the addition of an enhanced signal, three channels are established; an abdominal channel, a range gated enhanced abdominal channel, and an ultrasound channel. We would prefer to select them in that order for developing the fetal heart rate calculation. The abdominal channel signal comes in as signal A, FIG. 6. The range gated abdominal signal comes in as signal C, and the ultrasound signal comes in as signal B. These are all digital R detect signals. They come into the digital phase lock loop as previously described in FIG. 4, and the digital phase lock loop calculates the period and presents this to a tri state buffer. Following the signal flow from signal A in FIG. 6, the digital phase lock loop 98 presents period information to tri state buffer 105. Phase lock loop quality counter 99 verifies that the phase lock loop is tracking and establishes a degree of quality associated with that tracking. It outputs this quality measure to threshold level detector 100. If this quality measure exceeds this fixed threshold, detector 100 enables gated multi-vibrator 101. Gated multi-vibrator 101 then outputs a pulse periodically as long as the threshold level has been exceeded.

The output pulses from the gated multi-vibrator 101 cause relative quality counter 102 to count in a direction away from abdominal tracking and toward tracking either in the ultrasound or gated abdominal modes. Other inputs to relative quality counter 102 include the free running multi-vibrator 103 and pulse selection logic 122. Free running multi-vibrator 103 causes the relative quality counter to count in the direction of abdominal tracking. Pulse selection logic also causes the relative quality counter to count in direction of the abdominal tracking. The 3 digital phase look loops 98, 106 and 114 all operate essentially the same. The three phase lock loop quality counters 99, 100 and 115 also operate in the same way. The three threshold level detectors 100, 108 and 116 all operate in essentially the same way and the three gated multi-vibrators 101, 109 and 117 also operate in the same way and for the same purpose.

Relative quality counter 110 operates similar to relative quality counter 102, in that it has 3 inputs. The input from gated multi-vibrator 109 represents a measure of poor quality in the range gated abdominal signal and therefore causes the relative quality counter to count away from tracking the range gated abdominal signal and towards tracking the ultrasound signal. The input from gated multivibrator 117 represents a measure of poor quality in the ultrasound tracking signal and therefore its output causes relative quality counter 110 to count away from ultrasound tracking and towards range gated abdominal tracking. Also there is a bias input to the relative quality counter 110. This bias input is the free running multivibrator 103 which causes relative quality counter 110 to count towards the range gated abdominal tracking. The output of the relative quality counter 110 goes to operating mode in threshold logic 112. This circuit determines, based on previously set thresholds, which signal will be used to develop the fetal heart rate. If the range gated abdominal channel is selected, 112 operating threshold logic will turn on tri-state buffer 111 and shut off tri-state buffer 113. Tri-state buffer 111 will then present information to tri-state buffer 118.

Operating mode and threshold logic 112 controls pulse selection logic 122, which selects the better of the two channels, range gated abdominal or ultrasound, to be used to determine relative quality with the abdominal channel. This assures that the output of relative quality counter 102 is comparing the preferred channel, namely the abdominal channel, with the better of the other two channels. The output of relative quality counter 102 goes to 104 operating mode and threshold logic. This circuit, based on predetermined threshold, will select whether the abdominal period will be selected as the basis to calculate the fetal heart rate or either the range gated abdominal period or ultrasound period, whichever has been presented to tri-state buffer 118. If 104 operating mode threshold logic selects the abdominal channel as representing the best track on the fetal heart rate, then it will turn on the tri-state buffer 105 and shut off the tri-state buffer 118. Tri-state buffer 105 will then pass data representing the period from digital phase lock loop 98 to the divider period to rate 119. This loop is tracking and establishes a degree of quality associated with that tracking. It outputs this quality measure to threshold level detector 100. If this quality measure exceeds this fixed threshold, detector 100 enables gated multi-vibrator 101. Gated multi-vibrator 101 then outputs a pulse periodically as long as the threshold level has been exceeded.

The output pulses from the gated multi-vibrator 101 cause relative quality counter 102 to count in a direction away from abdominal tracking and toward tracking either in the ultrasound or gated abdominal modes. Other inputs to relative quality counter 102 include the free running multi-vibrator 103 and pulse selection logic 122. Free running multi-vibrator 103 causes the relative quality counter to count in the direction of abdominal tracking. Pulse selection logic also causes the relative quality counter to count in direction of the abdominal tracking. The 3 digital phase look loops 98, 106 and 114 all operate essentially the same. The three phase lock loop quality counters 99, 100 and 115 also operate in the same way. The three threshold level detectors 100, 108 and 116 all operate in essentially the same way and the three gated multivibrators 101, 109 and 117 also operate in the same way and for the same purpose.

Relative quality counter 110 operates similar to relative quality counter 102, in that it has 3 inputs. The input from gated multi-vibrator 109 represents a measure of poor quality in the range gated abdominal signal and therefore causes the relative quality counter to count away from tracking the range gated abdominal signal and towards tracking the ultrasound signal. The input from gated multivibrator 117 represents a measure of poor quality in the ultrasound tracking signal and therefore its output causes relative quality counter 110 to divider will then take the period and from it calculate the instantaneous fetal heart rate and then forward this information to digital display 120 and chart recorder 121.

Alternatively, if operating mode or threshold logic 104 determines from the relative quality counter input, that the abdominal channel does not represent the best tracking of the fetal heart signal, but instead one of the other two represents the best track, then operating mode and threshold logic 104 will shut off tri-state buffer 105 and turn on tri-state buffer 118. When tri-state buffer 118 is on it will pass through what is being presented to it via either tri-state buffer 111 or tri-state buffer 113. Therefore, if the best tracking is being done with the range gated abdominal signal, then the digital phase lock loop 106 period will be presented through the tri-state buffer 111, and through tri-state buffer 118, to the divider period of rate 119 as the basis of the fetal heart rate calculation. On the other hand, if the ultrasound tracking is determined to be the better and therefore should be the basis of the fetal heart rate calculaton, the period determined by digital phase lock loop 114 will be presented through tri-state buffer 113 and through tri-state buffer 118 to divider period of rate 119.

Operation

In FIGS. 10A-10C is an algorithm for switching between adbominal gated and ultrasound signals as the basis for fetal heart rate determination. First, a summary of the algorithm. Basically, each phase lock loop has a quality counter which determines a figure of merit of how well that phase lock loop is able to track the particular signal coming in on that channel. Each channel has associated with it a dedicated phase lock loop and associated quality counter. When this quality counter exceeds a certain threshold then it enables an input to one or more relative quality counters, which seek to order the tracking ability of the three channels. This ordering is in the sense of the best channel, the second best, and the third best.

The algorithm will track on the best channel. There are two relative quality monitors described in the algorithm in FIGS. 10A-10C. One of them, called relative quality monitor No. 1, determines the relative quality of the abdominal signal tracking versus the better of either gated abdominal or the ultrasound signal tracking. The second quality monitor, called relative quality monitor No. 2, determines the relative quality between the gated abdominal signal tracking and the ultrasound signal tracking. Thus, if quality monitor no. 1 says to use the abdominal channel, the abdominal channel will be used. Then if quality monitor no. 1 says don't use the abdominal channel, relative quality monitor no. 2 will determine which channel will be used.

At the top of the FIGS. 10A-10C we have block 122 which describes in detail the arithmetic operations performed on relative quality monitor 2. First relative quality monitor no. 2 is incremented by one for each 1.34 second period that the gated abdominal phase lock loop quality monitor exceeds 5. Second, this monitor is decremented by one for each 1.45 second period that the ultrasound phase lock loop quality monitor exceeds 5. These two operations provide a means of incrementing the quality monitor towards ultrasound tracking if the gated abdominal signal is of poor quality, and secondly, decrementing the quality monitor towards gated abdomnal tracking if the ultrasound quality is poor. Third, the quality monitor is decremented by one each 9.1 seconds. This provides a bias in the quality monitor such that if both channels are tracking equally well, then the relative quality monitor will select the gated abdominal channel.

Next the algorithm does a similar process with relative quality monitor no. 1. However in order to provide a correct subtract pulse, the status of relative quality monitor no. 2 must be known. Block 123 determines this by asking the question "Is the ultrasound tracking mode set?" If the answer is yes, then channel selection will be between abdominal channel and ultrasound channel. If the answer is no, then channel selection will be between abdominal channel and gated abdominal channel. Assuming the answer is "yes", block 124 causes 1 to be subtracted from relative quality monitor no. 1 for each 1.45 second period of the ultrasound phase lock loop quality monitor exceeds 5. Thus if the ultrasound tracking is relatively poor the relative quality monitor is decremented towards a decision to select abdominal tracking. If the answer to the block 123 question is no, block 125 causes 1 to be subtracted from relative quality monitor no. 1 for each 1.45 second period that the gated abdominal phase lock loop quality monitor exceeds 5. Thus if the gated abdominal tracking is relatively poor, the relative quality monitor no. 1 is decremented towards a decision to select abdominal tracking. From both blocks 124 and 125 the algorithm proceeds to block 126 which performs the arithmetic operations on relative quality monitor no. 1 These being to add 1 to relative quality monitor no. 1 for each 1.34 second period that the abdominal phase lock loop quality monitor exceeds 5, and to subtract 1 from the relative quality monitor 1, each 9.1 seconds.

The first causes relative quality monitor no. 1 to increment towards a decision to select either ultrasound or gated abdominal channel as a result of poor quality in the abdominal channel. The second causes relative quality monitor no. 1 to decrement towards a decision to track in the abdominal mode and this provides that bias which, if all channels are equal, will cause the entire system to track in the abdominal mode. Having adjusted the relative quality monitors, block 127 asks the question "Is relative quality monitor no. 1 greater than 4?" If the answer is no, block 128 asks the question "Is relative quality monitor no. 1 less than 3?" If the answer is yes, the algorithm wants the abdominal mode. If the answer is no, then the decision is within hysteresis range in which the algorithm wants to continue to track in the mode it is presently in.

Thus, if the relative quality monitor, no. 1, is not less than 3, block no. 129 asks the question "Is the abdominal tracking mode set?" If the answer is yes the algorithm has been tracking in the abdominal mode and will continue to track in the abdominal mode. If the answer to the block 129 question is no, the algorithm has not been tracking in the abdominal mode, and to determine the desired tracking mode the algorithm proceeds through blocks 137 and 138 and 139 which correspond to blocks 127, 128 and 129 respectively, as previously described.

If the results of blocks 128 and 129 determine that the abdominal mode should be used, block 130 then asks the question "Is the abdominal phase lock loop in restart?" If the answer is yes then we would want to disable display block 131 and return to the top of the diagram and continue in that loop until something changes, either one of the relative quality monitors crosses a threshold to change tracking to another mode or until the abdominal phase lock loop comes out of restart.

If the abdominal phase lock loop is not in restart, then block 132 sets the abdominal tracking mode, and block 133 and asks the question "Has the end of window transition occurred?" It is when the end of window transition occurs that sufficient information is available to determine which period measurement is a best estimate of the period and should be transmitted to the digital divider. Therefore if the end of window transition has not occurred, or is not occurring, then the algorithm returns to the top of the figure and continue in that loop until something changes or the window transition occurs. When the window transition occurs block 134 transfers the abdominal period to the digital divider where the fetal heart rate is calculated. Block 135 then enables the display and block 136 resets the ultrasound mode indicator on the chart recorder.

Returning to block 127, which asks the question "Is relative quality monitor no. 1 greater than 4?" If the answer is yes, then relative quality monitor no. 1 wants to track in the mode which has been determined by relative quality monitor no. 2 and the algorithm proceeds to block 137.

Blocks 137, 138 and 139 function as previously described for blocks 127, 128 and 129 respectively and result in tracking in the gated abdominal or ultrasound mode. If tracking is in the gated abdominal mode, the sequence picks up with block 140. If tracking is in the ultrasound mode, the sequence picks up with block 147. Block 140 asks the question, "Is the gated abdominal phase lock loop in restart." If the answer is yes the algorithm disables the display, returns to the top and continues in that loop until something changes or until the gated abdominal phase lock loop comes out of restart. When the phase lock loop is not in restart block 142 resets both the abdominal and ultrasound tracking modes thereby indicating that the algorithm is operating in the gated abdominal tracking mode. From that point the algorithm proceeds through blocks 143, 144, 145, 146 which function as previously described for blocks 133, 134, 135 and 136 respectively.

Block 146 resets the ultrasound mode indicator on the chart recorder thereby giving an abdominal tracking mode indication even though tracking is actually in the gated abdominal mode. An alternate implimentation could have seperate indications for each mode.

Block 137, asks the question "Is relative quality monitor no. 2 greater than 4?" If the answer is yes, then block 147 asks "Is the ultrasound phase lock loop in restart?" If it is, display is disabled in block 148. If it is not, then block 149 sets the ultrasound tracking mode and resets abdominal tracking mode. From that point the algorithm proceeds through blocks 150, 151, 152, and 153 which functions as previously described for blocks 133, 134, 135, and 136 respectively.

The relative quality monitors are limited to the range between 0 and 7. If a relative quality monitor indicates a 0, 1, or 2, it is definitely indicating that tracking should occur in one mode. If that monitor is indicating a number 5, 6 or 7 then it is indicating that we definitely should track in another mode. However, there is a hysteresis in the threshold between tracking in these modes, and this occurs if the relative quality monitor indicates either 3 or 4. In this instance we would want to continue to track in the mode in which we had previously been tracking.

INTERLACING MCG AND ECG SIGNALS

The diagram in FIG. 11 illustrates substituting ultrasound events in place of fetal ECG signals which have been deleted by maternal gates. Since the maternal and fetal QRS signals are asynchronous, from time to time the fetal QRS complex occurs simultaneously with the maternal QRS complex. As shown in Patent 428, a maternal gate is generated by the maternal QRS complex which deletes any signal appearing in the fetal channel, at that time. If fetal QRS complexes are deleted by the maternal gate the phase lock loop will fill in these fetal signals by assuming they occurred precisely where they were anticipated, namely in the center of the window. Naturally, this is an assumption which is not always correct and therefore introduces a small error in the abdominal tracking mode. With the simultaneous monitoring of ultrasound and abdominal events it becomes possible to fill in the fetal signals, which were deleted by the maternal gate, by using the information which exists in the ultrasound channel. In order for this to work, the processed ultrasound signal B must be aligned with the R-detect signal. Since it takes some time for the ultrasound signal to be processed through the correlator, a delay circuit 199 inserts a delay between the R-detect signal A and the phase lock loop which is about to process that signal.

Blocks 202 through 208 in FIG. 1 correspond with blocks 47 through 53 in FIG. 5 and operate in a similar fashion. Period measurements are made on the delayed R-detect signal output for the circuits 199. When one of the following three situations occur, the ultrasound is used to fill in for missing R-detect signals and develop a substitute period measurement. The three conditions are, first that there is no abdominal fetal signal detected in this window, secondly that there is no abdominal event detected in either this window or the last window, and finally that there is no abdominal fetal event detected in the last window. In the first instance, the substitute period measurement Block 200 will measure the period from the last abdominal event detected within the window to the processed ultrasound event detected within the next window. In the second instance, the substitute period measurement Block 200 will measure the time between the processed ultrasound event detected in the last window and the processed ultrasound event detected in this window. And in the third instance, the substitute period measurement Block 200 will measure the period between the ultrasound event detected in the last window and the abdominal fetal event which has been detected in this window.

Block 202, selection logic, then determines if any of these three cases applies. If one of them does, it will take the period measurement information from blocks 200 and pass it on to Blocks 204, 205 and 207. If none of these situations existed, then the abdominal period measurement developed in Block 201 is a correct measurement and the selection logic 202 will pass this information on to Blocks 204, 205 and 207.

In FIG. 12, a signal enhancement by multiplication circuit block diagram is shown. The basic idea behind this block diagram is the known relationship between the individual ultrasound Doppler events and the Doppler events and the QRS complex. Although there may be three, four, or as many as a half dozen individual Doppler events detected in a single fetal heart period, one of these events typically occurs just shortly before the QRS wave occurs. By delaying the ultrasound Doppler wave form, we can cause this Doppler event to occur simultaneously with the QRS complex. Now, if we multiply the abdominal signal by the delayed ultrasound Doppler event wave form we can enhance the abdominal signal in the immediate vicinity of the ultrasound Doppler peaks and reduce the abdominal signal in between those peaks. This results in a significant improvement in the signal to noise ratio of the system. Thus, fetal QRS complexes can be detected by an amplitude discrimination technique, where none were detectable before.

Input F is the ultrasound Doppler wave form from FIG. 4. This signal is first routed through an automatic gain control amplifier to normalize the amplitude of the signal and thus permit us to operate over a much wider dynamic range of ultrasound Doppler events. The output of the ACG amplifier goes to a delay which, to a first approximation can be fixed. However, as described in FIG. 13, it may be a delay which varies as a function of the heart rate. To provide better alignment of the ultrasound and abdominal signals, the output of the delay goes to analog multiplier 212 is signal E, which comes from FIG. 3, and is the fetal channel abdominal signal after the maternal QRS complexes have been deleted. These two signals are multiplied in analog multiplier 212 and the output routed to amplifier 213 which provides a low impedance output voltage signal to Blocks 214 through 216 which together with 217 comprise an amplitude detect circuit as previously described in FIG. 3.

A block diagram is shown in FIG. 13, for controlling the delay Block 211 in FIG. 12 as a function of heart rate. Signals I and J in FIG. 12 correspond to the input signal I and the output signal J in FIG. 13. Signal H comes from the output of the divider period to rate block in FIG. 9. Signal H is a digital representation of the fetal heart rate and is converted to an anolog signal in D to A converter 220. This signal is then smoothed in filtered 221 and used to control an oscillator frequency in voltage controlled oscillator 222. By varying the frequency of this oscillator, the rate A to D conversion in Block 223 can be speeded up or slowed down and the rate at which data is shifted through shift register 224 can likewise be speeded up or slowed down and the reconversion to analog and D to A convertor 225 can keep pace. Hence the delay in the signal from input I to J will reduce as the oscillator frequency is increased and this delay will increase as the oscillator frequency is slowed down. Thus, the delay is varied as a function of the fetal heart rate.

In FIG. 14 a monitor signals from a biological object is illustrated. Two or more say K, input signals representative of one or more, selected charecteristic, such as pulse, blood pressure, phonocardiograph and/or an ECG, may be processed to produce M immediate signals, N output signals may be selected from Re input and intermediate signals to provide desired indications of Such a selected charecteristic.

Here the K inputs are indicated at 320 coupled from a biological object to a Biological signals Monitor 321 where the signals may be individually processed or interprocessed to provide M immediate signals from which N output signals indicative of said one, or more selected charecteristics.

SUMMING—ECG and MCG

The circuit block diagram in FIG. 15 illustrates signal enhancement by cross correlation and signal summing to produce an enhanced FHR signal. For a given heart rate, the time relationship between the Doppler events in that heart cycle and the QRS complex can be determined. Typically in a heart cycle there are three Doppler events of significance. By delaying the ultrasound wave form by the amount of the time difference between the first and second Doppler events and adding it to the undelayed ultrasound wave form, two of the Doppler events will be time coincident and add together. Finally, if the ECG waveform is delayed to cause time coincidence between the R-wave and the three summed Doppler events, further enhancement results. The resulting summation waveform will contain a multitude of small peaks and one large peak where all of the Doppler events and the R-wave ad up, and this large peak will correspond to a detected heart beat. From these enhanced peaks, the cardiac period can be determined and, from that, the fetal heart rate. The block diagram for this concept is given in FIG. 15. Inputs to FIG. 15 are signal E, which is the analog ultrasound signal from FIG. 4. These signals are routed through controlled delays 1,2, and 3 shown in the diagram as blocks 230, 231 and 232. These delays are controlled by blocks 238, 239 and 240 in which the delays are computed. The delayed signals are added together with an undelayed reference signal in summing amplifier 233. The inputs to this amplifier may be weighted in any fashion to optimize the signal processing. The output of the summing amplifier is routed to peak detector 234, which detects the maximum peak and the transfers a pulse corresponding to this peak to block 235, which computes the fetal heart period. The output from peak detecter 234 also goes to a digital phase lock loop, such as shown in FIG. 9, for further processing which ultimately results in the fetal heart rate display. Each time a period is computed in Block 235 that period is stored in Block 236 against the possibility that the next period will not be within an acceptable range. The outputs of 235 and 236 go to selection logic 237 which determines whether the newly computed period is an acceptable period or whether the delays should be computed based on previously stored period in 236. The output selection logic of 237 is input to Blocks 238, 239 and 240 which compute the delays 1, 2 and 3 respectively.

While there has hereinbefore been described what are now considered to be preferred embodiments and methods of the invention, it will be apparent that many modifications and changes may be made, thereto, without departing from the true scope of the invention. All such changes and modifications, therefore, are deemed to be a part of this invention.

What is claimed is:

1. Apparatus for generating an output signal indicative of the rate of fluctuation of a human fetal heart, comprising:
   (A) means for coupling an input electrocardiographic signal from a fetus-carrying female human to said apparatus;
   (B) means for processing said electrocardiographic signal to produce a first electric signal indicative of the rate of fluctuation of the heart of said fetus;
   (C) means for coupling an input mechanical cardiographical signal from said human to said apparatus;
   (D) means for processing said mechanical cardiographical signal to produce a second electric signal indicative of the rate of fluctuation of the heart of said fetus; and,
   (E) means for comparing said electric signals for choosing the better of the two signals to produce an output signal best indicative of said fetal heart rate.

2. The apparatus of claim 1, wherein: said first and second electric signals are continuously monitored continuously to produce an output signal best indicative of said fetal heart rate.

3. The apparatus of claim 1, wherein: said mechanical signal is sonic.

4. The apparatus of claim 3, wherein: said mechanical coupling means includes means adapted to generate a sonic beam directed to said fetal heart; and means for heterodyning said beam and input sonic signals for deriving said second electric signal proportional to the difference of the Doppler frequency between transmitted and reflected energy.

5. The apparatus of claim 1, wherein: means are included for cross-correlating said electric signals.

6. The apparatus of claim 1, wherein: means are included for verifying each of said electric signals relative to said fetal heart rate.

7. The apparatus of claim 1, wherein: means are included for processing said electric signals in accordance with a selected function to produce an output signal superior to either one of the said electric signals relative to said fetal heart rate.

8. The apparatus of claim 7, wherein: means are included for adding said electric signals.

9. The apparatus of claim 7, wherein: means are included for multiplying said electric signals.

10. The apparatus of claim 1, wherein: means are included for biasing said output signal in favor of said first electric signal.

11. The apparatus of claim 1, wherein: means are included for varying the time of occurrence of one said electric signal relative to the other.

12. The apparatus of claim 1, wherein: means are included for disabling said generate means only when said electrocardiographic signal has been selected.

* * * * *